United States Patent [19]

Suzuki

[11] 4,000,163

[45] Dec. 28, 1976

[54] PALLADIUM CATALYZED ISOMERIZATION OF ALKENYL SUCCINIC ANHYDRIDE AND PALLADIUM CATALYZED REACTION OF ALKENYL SUCCINIC ANHYDRIDE AND OLEFINES PRODUCING ALPHA-ALKYL, β-ALKENYL SUCCINIC ANHYDRIDE

[75] Inventor: Shigeto Suzuki, San Francisco, Calif.

[73] Assignee: Chevron Research Company, San Francisco, Calif.

[22] Filed: Sept. 15, 1975

[21] Appl. No.: 613,598

[52] U.S. Cl. .................................... 260/346.8 R
[51] Int. Cl.² .................................... C07D 307/60
[58] Field of Search ............ 260/346.8, 346.3, 326

[56] References Cited

UNITED STATES PATENTS 2,764,597  9/1956  Barney .......................... 260/346.3

*Primary Examiner*—Henry R. Jiles
*Assistant Examiner*—Bernard Dentz
*Attorney, Agent, or Firm*—G. F. Magdeburger; John Stoner, Jr.; W. Keith Turner

[57] ABSTRACT

A process for preparing alkyl maleic anhydrides which comprises heating a lower alkenyl succinic anhydride in the presence of a catalytic amount of a palladium salt in combination with a weakly basic material under conditions effective to isomerize the alkenyl succinic anhydride.

13 Claims, No Drawings

PALLADIUM CATALYZED ISOMERIZATION OF ALKENYL SUCCINIC ANHYDRIDE AND PALLADIUM CATALYZED REACTION OF ALKENYL SUCCINIC ANHYDRIDE AND OLEFINES PRODUCING ALPHA-ALKYL, β-ALKENYL SUCCINIC ANHYDRIDE

BACKGROUND OF THE INVENTION

This invention relates to the preparation of select alkyl maleic anhydrides from alkenyl succinic anhydrides. Alkyl maleic anhydrides prepared in accordance with this invention are useful intermediates in the preparation of alpha-alkyl-beta-alkenyl succinic anhydrides which are known to be useful paper sizing agents and gasoline detergent additives.

A variety of processes for the preparation of alkenyl succinic anhydrides have been known and used for many years. For instance, U.S. Pat. No. 2,411,215, granted Nov. 16, 1946, and U.S. Pat. No. 3,819,660, granted June 25, 1974, describe the 1,2-addition reaction of monoolefins with maleic anhydride to prepare the corresponding alkenyl succinic anhydride. In general, the reaction proceeds according to the reaction scheme:

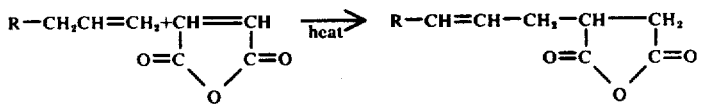

While alkenyl succinic anhydrides are useful products, there is a continuing need to develop a simple process for preparing alkyl maleic anhydrides. Toward this aim, it would be desirable to develop a means of isomerizing the alkenyl exocyclic double bond of alkenyl succinic anhydrides back into the anhydride ring to form alkyl maleic anhydrides.

The use of various acid catalysts to isomerize aliphatic alkenes is described in the prior art. For instance, Noller (Ed.), "Chemistry of Organic Compounds 3rd", W. B. Saunders (1966) describes the acid-catalyzed interconversion of 1-butene and cis- and trans-2-butene. Additionally, Noller discloses the thermally induced rearrangement of itaconic anhydride to citraconic anhydride.

SUMMARY OF THE INVENTION

The process of the present invention comprises heating a lower alkenyl succinic anhydride of the formula

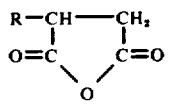

wherein R is an alkenyl group containing from about 3 to 7 carbon atoms, at a temperature below about 250° C in the presence of a catalytic amount of a palladium salt in combination with a weakly basic material.

DETAILED DESCRIPTION OF THE INVENTION

The present invention relates to the discovery that select alkyl maleic anhydrides can be prepared from corresponding alkenyl succinic anhydrides utilizing as a catalytic system from about 0.1 to 15.0%, by weight, of a palladium salt in combination with from about 0.5 to 15.0%, by weight, of weakly basic material.

The alkenyl succinic anhydrides suitable for use in the practice of this process can be obtained by a variety of well-known reactions. In general, alkenyl succinic anhydrides can be prepared by thermal condensation of maleic anhydrides with monoolefins. U.S. Pat. Nos. 2,411,215 and 3,819,660, previously mentioned, describe typical preparations.

More particularly, alkenyl succinic anhydrides suitable for use herein are characterized by an alkenyl substituent containing from about 3 to 7, preferably from about 3 to 5, carbon atoms. It has been found that the higher-chain-length alkenyl succinic anhydrides, containing greater than about 7 carbon atoms in the alkenyl group, when heated in the presence of an isomerization catalyst, predominantly yield the alkenyl succinic anhydride isomers and only minor amounts of the desired maleic anhydride isomer. Accordingly, alkenyl succinic anhydrides having greater than about 7 carbon atoms in the alkenyl substituent are unsatisfactory for use herein.

Illustrative alkenyl succinic anhydrides suitable for use in the preparation of alkyl maleic anhydrides include, for example, allyl succinic anhydride, butenyl succinic anhydride, hexenyl succinic anhydride, heptenyl succinic anhydride, 4,4-dimethyl pentenyl succinic anhydride, 3,4-dimethyl pentenyl succinic anhydride, and the like. It will be apparent to those skilled in the art that the position of the alkenyl double bond is not critical to the isomerization; however, as the double bond is positioned farther than the 2,3 position from the anhydride ring the process will produce a mixture of products in which the double bond is predominantly in the exocyclic positions thereby reducing the conversion to alkyl maleic anhydride. Accordingly, alkenyl succinic anhydrides having the exocyclic double bond in the 1,2 or 2,3 position are preferred. Illustrative preferred alkenyl succinic anhydrides include, for example, allyl succinic anhydride and 2-butenyl succinic anhydride.

It has been found that only select Group VIII noble transition metal systems will efficiently catalyze the desired isomerization. The present process relates to the isomerization of alkenyl succinic anhydrides in the presence of catalytic amounts of a palladium salt in combination with a weakly basic material.

The amount of palladium salt and the amount of base present in the system can vary over a wide range. For example, amounts of each component ranging from about 0.1 to about 15.0%, by weight of alkenyl succinic anhydride, are satisfactory, and amounts ranging from about 1.0 to about 5.0% are preferred. In general, the palladium salt is used at the lower levels of concentration, whereas the basic materials are used at the higher levels of concentration.

Suitable palladium salts include, for example, organic and inorganic salts of the formula $$Pd(L)_n(X)_m$$

wherein L is nonionic organic ligand or water complexed to the palladium; X is an inorganic anionic ligand bound to the palladium; $n$ is 0 to 5; $m$ is 0 to 3; and $m+n$ is 3 to 6. It is understood, of course, that $m+n$ represents the coordination number of palladium, i.e., three-, four-, five- or six-coordinate, and that the $m$ represents the valence or oxidation state of the palladium moiety. Additionally, the palladium salts depicted represent only the empirical composition which may exist in a dimeric or polymeric form.

In accordance with the above formula, suitable nonionic ligands complexed to the palladium, L, include, for example, water, carbon monoxide, olefins, organophosphines, organoarsines, organostibines, and organobismuthines. Suitable anionic ligands bound to palladium, X, include, for example, halides, nitrite, and hydride.

Preferred L ligands include carbon monoxide and hydrocarbyl phosphines such as triphenylphosphines and trialkylphosphines. Preferred X ligands include halides such as chloride, bromide, and iodide.

Illustrative palladium salts suitable for use herein include palladium halides such as $PdCl_2$, $PdCl_2 \cdot 3h_2O$, $PdBr_2$ and $PdI_2$; palladium carbonyl halides such as $Pd(CO)CL_2$, $Pd(CO)_2Cl_2$, and $Pd(CO_2I_3$; palladium carbonyls such as $Pd(CO)_4$ and $[Pd(CO)_4]_3$, palladium organophosphines such as $Pd[P(C_6H_5)_3]_4$, $Pd[P(C_6H_5)_3]_3$, $PdCl_2[P(CH_3)_3]_2$ and $Pd(NO_3)_2[P(CH_3)_2]_2$; and palladium salts such as $PdCl_2[AS(CH_2)_3]_2$ and $PdI_2[Sb(C_6H_5)_3]_2$.

The preferred palladium salt is palladium dichloride.

It has been found that, when used alone, the above-described palladium salts isomerize the alkenyl double bond of most alkenyl succinic anhydrides one step only. Accordingly, the palladium salt is utilized in combination with a weakly basic material to promote isomerization. Promoting basic materials suitable for use in combination with the palladium salts include both soluble and insoluble organic and inorganic bases having a $pK_b$ in water of from 2 to about 10.

Suitable soluble bases include, for example, organic tertiary amines and phosphines. A thorough discussion of organic amines and phosphines is found at Chapter 24 of Noller's "Chemistry of Organic Compounds 3rd". Illustrative suitable organic tertiary amines include alkyl amines such as trimethylamine, methylethyl-i-propylamine and tributylamine; and aromatic tertiary amines such as N,N-dimethyl toluidine, phenyleneN,N-dimethylaniline, methylenediamine, pyridine, guinoline, and methyl diphenylamine. Illustrative suitable phosphines include phenyl dimethylphosphine, diphenyl propylphosphine, and triphenylphosphine.

Suitable insoluble bases include, for example, the basic ion exchange resins such as polypropylene-vinyl-pyridine graft copolymers, aminated bivinylbenzene-vinylbenzylchloride copolymers, and the like.

It is apparent that the choice of base is not limited to specific materials; however it has been found that dimethylaniline and triphenylphosphine are particularly well suited for combination with the palladium salts.

The isomerization process of the invention is conducted in a fluid phase, i.e., either gaseous or liquid phase, in the presence or in the absence of an inert diluent. The process is carried out by either sequentially or simultaneously contacting the alkenyl succinic anhydride with the palladium salt and basic material, depending upon the selection of either a soluble or insoluble base. It has been found that when soluble bases are employed it is preferable to add the base after the initial isomerization has been effected using the palladium salt; otherwise these bases somewhat deactivate the palladium salt and isomerization is slowed. On the other hand, insoluble bases may be added initially without deactivating the palladium salt.

Although isomerization will proceed at moderate temperatures and pressures, for most practical applications reaction temperatures ranging from about 50° to about 250° C are satisfactory, and temperatures of from about 70° to about 230° C are preferred. Within this temperature range, reaction time will vary from a few minutes to a few hours. The process is conducted at or above atmospheric pressure; pressures from about 1 atmosphere to 200 atmospheres are satisfactory.

At the conclusion of isomerization, equilibrium is reached between the various exocyclic alkenyl succinic anhydrides and alkyl maleic anhydride. Alkyl maleic anhydride can be recovered by conventional means such as distillation, and the alkenyl succinic anhydrides can be recycled for further isomerization.

A principal advantage of the present process resides in the relatively high yield of alkyl maleic anhydride isomer obtained at equilibrium. While yields will vary depending upon such factors as the choice of starting material, catalyst, and temperature of reaction, it has been found that yields on the order of at least 40%, by weight, of alkyl maleic anhydride are typical.

Another advantage of the present process for preparing alkyl maleic anhydrides is that a second olefinic moiety may be added to the unsubstituted ring carbon atom, thereby providing a simple snythetic route to alpha-alkyl-beta-alkenyl succinic anhydrides, useful as detergent and paper-sizing compounds. The over-all reaction process typically proceeds according to the scheme:

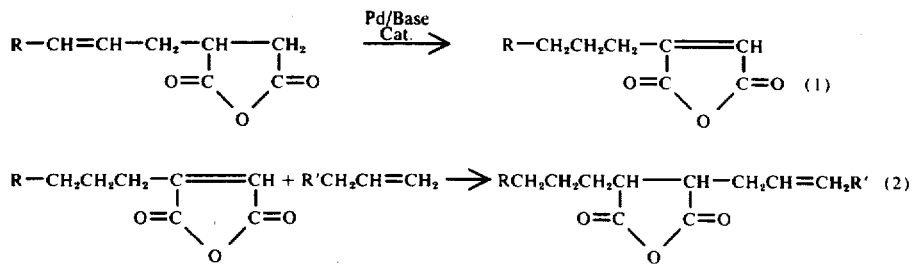

Although schematically presented as a two-step reaction, in practice alpha-alkyl-beta-alkenyl succinic anhydrides can be prepared in accordance with this invention by heating a mixture comprising an alkenyl succinic anhydride and an olefin, at a temperature below about 250° C in the presence of a catalytic amount of a palladium salt in combination with a basic material, as described above. This process is believed to kinetically favor isomerization to form the intermediate maleic anhydride, thereby providing high yields of desired product.

In the above process, the second olefin molelcule may be of any chain length; however, in many applications olefins containing an average of at least 8 carbon atoms are preferred.

EXAMPLES

The following examples illustrate the practice of this invention, but are not intended to be limiting thereof.

EXAMPLE I

Isomerization of Allyl Succinic Anhydride Using PdCl$_2$/Soluble Base 10 g of allyl succinic anhydride were placed in a reaction vessel. 0.1 g of palladium dichloride (1.0% by weight based on anhydride) were added with constant stirring. The reaction mixture was heated to a temperature of 110° C for 190 minutes.

0.5 g of dimethylaniline (5.0% by weight based on anhydride) were added. The reaction was allowed to proceed 60 additional minutes at 110° C, at which time analytical analysis confirmed a product distribution of 34.9% propyl maleic anhydride and the balance propenyl succinic anhydrides and unknown. The reaction was completed after a second 60-minute period at 110° C (a total of 310 minutes). A second product analysis confirmed 45.3% propyl maleic anhydride and the balance propenyl succinic anhydrides and unknown.

An equivalent amount of butenyl succinic anhydride, hexenyl succinic anhydride, heptenyl succinic anhydride, 4,4-dimethyl pentenyl succinic anhydride and 3,4-dimethyl propenyl succinic anhydride, respectively, is substituted for allyl succinic anhydride and isomerized in a like fashion.

An equivalent amount of palladium tetracarbonyl, palladium dibromide, and palladium dicarbonyl dichloride, respectively, is substituted for palladium dichloride in the above procedure and substantially equivalent results are achieved.

An equivalent amount of trimethylamine, N,N,N',N'-tetramethyl-phenylenediamine and dimethyl toluidine, respectively, is substituted for dimethylaniline in the above procedure and substantially equivalent results are achieved.

EXAMPLE II

Isomerization of Allyl Succinic Anhydride Using PdCl$_2$/Soluble Base 2.0 g of allyl succinic anhydride were placed in a reaction vessel. 0.02 g of palladium dichloride (1.0% by weight based on anhydride) were added with constant stirring. The reaction mixture was heated to a temperature of 110° C for 30 minutes.

0.1 g of triphenylphosphine (5.0% by weight based on anhydride) were added. The reaction was allowed to proceed 30 additional minutes at 100° C, at which time analytical analysis confirmed a product distribution of 47.3% propyl maleic anhydride and the balance propenyl succinic anhydrides and unknown. The reaction was complete after a total of 210 minutes at 100° C. A second product analysis confirmed 58.1% propyl maleic anhydride and the balance alkenyl succinic hydrides and unknown.

An equivalent amount of butenyl succinic anhydride, hexenyl succinic anhydride, heptenyl succinic anhydride, 4,4-dimethyl pentenyl succinic anhydride and 3,4-dimethyl propenyl succinic anhydride, respectively, is substituted for allyl succinic anhydride in the above procedure and isomerized in a like fashion.

An equivalent amount of palladium tetracarbonyl, palladium dibromide, and palladium dicarbonyl dichloride, respectively, were substituted for palladium dichloride in the above procedure, and substantially equivalent results are achieved.

An equivalent amount of phenyl dichlorophosphine and diphenyl chlorophosphine is substituted for triphenylphosphine in the above procedure, and substantially equivalent results are achieved.

EXAMPLE III

Isomerization of Allyl Succinic Anhydride Using PdCl$_2$/Insoluble Base 2.0 g of allyl succinic anhydride were placed in a sealed reaction vessel. 0.02 g of palladium dichloride (1.0% by weight of anhydride) were added with constant stirring. The reaction mixture was heated to a temperature of 150° C for 15 minutes.

0.3 g of a graft copolymer of polypropylene and vinylpyridine (15% by weight based on anhydride) were added. The reaction was allowed to proceed for 30 additional minutes at 150° C, at which time analytical analysis confirmed a product distribution of 20% propyl maleic anhydride and the balance propenyl succinic anhydrides and unknown. The reaction was allowed to proceed for 30 additional minutes at a temperature of 150° C, at which time a second product analysis confirmed 34.0% propyl maleic anhydride and the balance propenyl succinic anhydrides and unknown. Finally, the reaction was allowed to proceed an additional 120 minutes (for a total of 195 minutes) at 200° C, at which time a third product analysis confirmed 51.0% propyl maleic anhydride and the balance propenyl succinic anhydrides and unknown.

EXAMPLE IV

Preparation of alpha-Alkyl-beta-Alkenyl Succinic Anhydrides 1.30 g of allyl succinic anhydride, 2.25 g of 1-octene and 0.025 g of hydroguinone are placed in a sealed reaction vessel. 0.015 g of palladium dichloride and 0.2 g of a graft copolymer of polypropylene and vinylpyridine are added. The reaction mixture is heated to a temperature of 230° C and allowed to proceed for 24 hours. Analyses of the reaction product by gas chromatography shows substantial conversion of initially added allyl succinic anhydride to alpha-propyl-beta-octenyl succinic anhydride.

A duplicate run without the added palladium dichloride-copolymer of polypropylene and vinylpyridine gave hardly any reaction.

What is claimed is:

1. A process for preparing alkyl maleic anhydride which comprises heating an alkenyl succinic anhydride of the formula

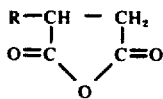

wherein R is alkenyl containing 3 to 7 carbon atoms at a temperature below about 250° C in the presence of a catalytic amount of a palladium salt of the formula $$Pd(L)_n(X)_m$$

wherein L is a nonionic organic ligand or water complexed to the palladium; X is an inorganic anionic ligand bound to the palladium; $n$ is 0 to 5; $m$ is 0 to 3; and $m + n$ is 3 to 6 in combination with a weakly basic material having a $pK_b$ of from 2 to about 10.

2. A process according to claim 1 wherein said process is conducted at a temperature in the range from about 50° to about 250° C.

3. A process according to claim 1 wherein succinic anhydride is allyl succinic anhydride.

4. A process according to claim 1 wherein said palladium salt is palladium dichloride.

5. A process according to claim 1 wherein said basic material is soluble.

6. A process according to claim 5 wherein said soluble base is an organic tertiary amine.

7. A process according to claim 6 wherein said amine is dimethylaniline.

8. A process according to claim 5 wherein said soluble basic material is an organic phosphine.

9. A process according to claim 8 wherein said phosphine is triphenylphosphine.

10. A process according to claim 1 wherein said base is insoluble.

11. A process according to claim 10 wherein said base is is basic ion-exchange resin.

12. A process according to claim 11 wherein said base is a polypropylene-vinylpyridine graft copolymer.

13. A process for preparing alpha-alkyl-beta-alkenyl succinic anhydride which comprises heating a mixture comprising an alkenyl succinic anhydride of the formula

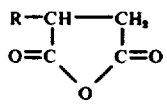

wherein R is alkenyl containing 3 to 7 carbon atoms, and an olefin at a temperature below about 250° C in the presence of a catalytic amount of a palladium salt of the formula $$Pd(L)_n(X)_m$$

wherein L is a nonionic organic ligand or water complexed to the palladium; X is an inorganic anionic ligand bound to the palladium; $n$ is 0 to 5; $m$ is 0 to 3; and $m + n$ is 3 to 6 in combination with a weakly basic material having a $pK_b$ of from 2 to about 10.

* * * * *